United States Patent [19]
Smith, Sr.

[11] Patent Number: 6,131,816
[45] Date of Patent: Oct. 17, 2000

[54] DATA SYSTEM WITH SUPPORT SURFACES FOR RECIPROCATING DATA HEAD

[75] Inventor: Malcolm G. Smith, Sr., Gold Hill, Oreg.

[73] Assignee: UltraCard, Inc., Campbell, Calif.

[21] Appl. No.: 09/113,783

[22] Filed: Jul. 10, 1998

Related U.S. Application Data

[63] Continuation of application No. 09/105,696, Jun. 26, 1998, abandoned, which is a continuation-in-part of application No. 07/871,447, Apr. 21, 1992, abandoned, which is a continuation-in-part of application No. 07/342,217, Apr. 24, 1989, Pat. No. 5,107,099.

[51] Int. Cl.[7] .................................................. G06K 13/00
[52] U.S. Cl. ........................ 235/475; 235/441; 235/486; 235/479; 235/449
[58] Field of Search .................................. 235/475, 441, 235/486, 483, 485, 479, 449, 482

[56] References Cited

U.S. PATENT DOCUMENTS

| | | | |
|---|---|---|---|
| 4,197,988 | 4/1980 | Moss et al. | 235/449 |
| 4,209,811 | 6/1980 | Blazevic | 360/78 |
| 4,581,523 | 4/1986 | Okunu | 235/479 |
| 4,774,618 | 9/1988 | Raviv | 360/133 |
| 4,897,533 | 1/1990 | Lyszczarz | 235/487 |
| 5,099,111 | 3/1992 | Takakura et al. | 235/475 |
| 5,107,099 | 4/1992 | Smith | 235/449 |
| 5,521,774 | 5/1996 | Parks et al. | 360/81 |

*Primary Examiner*—Donald Hajec
*Assistant Examiner*—Daniel S Felten
*Attorney, Agent, or Firm*—Townsend & Townsend & Crew LLP

[57] ABSTRACT

A data system (1) includes a credit card type substrate (3) and a data unit (2). The substrate has first and second edges (28, 30) and a data surface region (26) between the edges. The data unit includes a base (4), a substrate support (60) mounted to the base for controlled movement along a first path (14), and a data head driver (6), also mounted to the base, including a data head which reciprocates along a second path (10) oriented perpendicular to the first path. The data head contacts the data surface region on the substrate and first and second data head support surfaces (120, 122) located at opposite ends of the second path adjacent to the first and second edges of the substrate. The data head support surfaces and the data surface region are coplanar. The data unit also includes a substrate feeder (16), which delivers the substrate to and removes the substrate from the substrate support, and a substrate positioner (68, 70, 82, 94, 98), which properly positions the substrate on and secures the substrate to the substrate support.

26 Claims, 7 Drawing Sheets

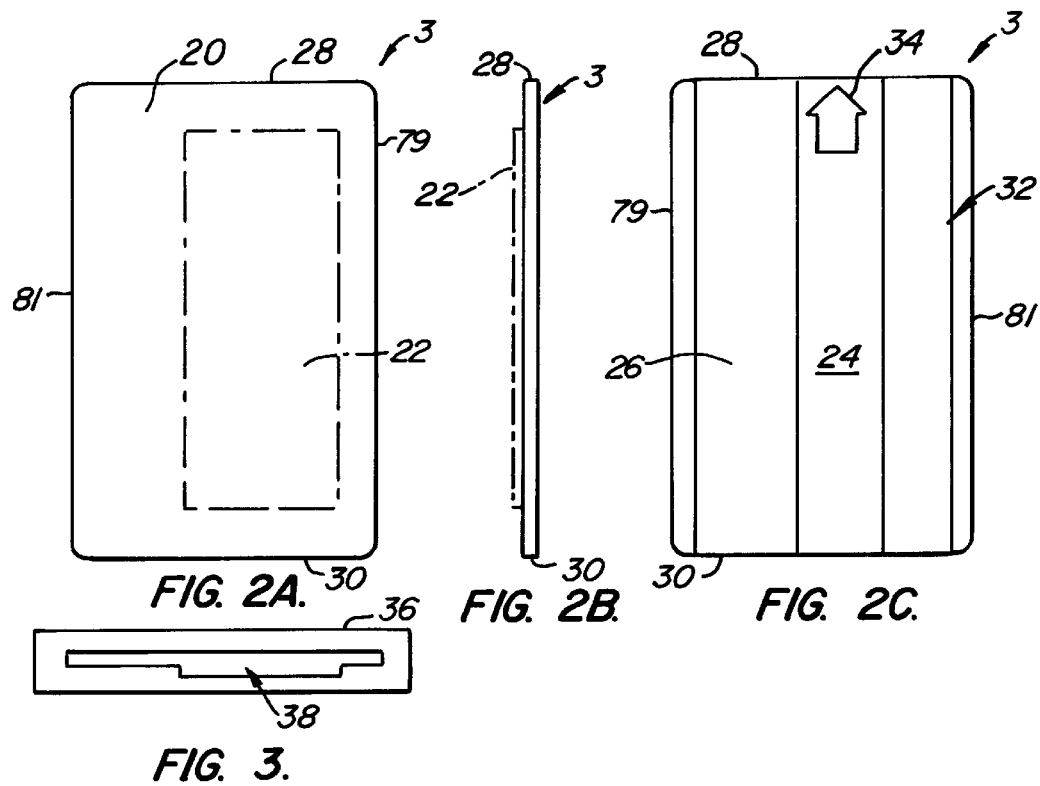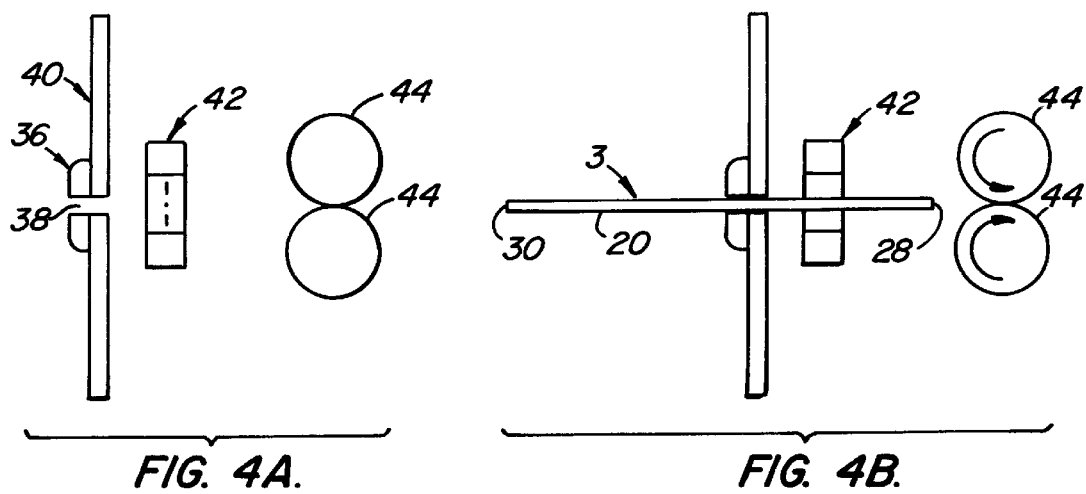

6,131,816

DATA SYSTEM WITH SUPPORT SURFACES FOR RECIPROCATING DATA HEAD

CROSS-REFERENCE TO RELATED APPLICATIONS

This application is a continuation of U.S. patent application Ser. No. 09/105,696, filed Jun. 26, 1998, now abandoned, which is a continuation-in-part of U.S. patent application Ser. No. 07/871,447, filed Apr. 21, 1992 (now abandoned), which in turn is a C-I-P of Ser. No. 07/342,217 filed Apr. 24, 1989, now U.S. Pat. No. 5,107,099.

BACKGROUND OF THE INVENTION

Digital data is stored in many forms. One data storage device uses spinning disks having a magnetic surface containing the digital data. The disks typically spin at a high rate of speed with the various tracks of data accessed by a radially movable data head. Another type of data storage device is the credit card having a magnetic stripe along one surface. However, such cards have limited storage capacity because of the nature of the magnetic stripe and the method of recording data onto the magnetic stripe.

SUMMARY OF THE INVENTION

The present invention is directed to a data system especially suited for use with credit card-type substrates which permits much more data to be written onto and read from the substrate than available with credit cards with conventional magnetic stripes.

The data system includes broadly a substrate, such as a credit card type substrate, and a data unit. The substrate has first and second edges and a data surface region between the edges. The data surface region is preferably plated or sputtered with nickel-cobalt as opposed to conventional credit cards which use ferrous oxide. The data unit includes a base supporting several components. A substrate support, which supports the substrate, is mounted to the base for controlled movement along a first path. The first path can be straight or curved. A data head drive is mounted to the base and includes a data head reciprocally movable along a second path. The first and second paths are generally transverse, typically perpendicular, to one another. The data head includes a data head surface which contacts the data surface region on the substrate. The data unit also includes first and second data head support surfaces positioned along the second path adjacent to the first and second edges of the substrate. The data head surface also contacts the first and second data head support surfaces as the data head moves along the second path.

The data head support surfaces are preferably coplanar with the data surface region of the substrate. This provides a smooth transition for the data head between the data surface region and the data head support surfaces. The use of the data head support surfaces provides a region for the data head to accelerate and decelerate at each end of a pass over the data surface region so the data head can move over the data surface region at a constant surface speed.

The invention may also include a substrate handler including a substrate feeder, which delivers a substrate to and removes the substrate from the substrate support, and a substrate positioner, which automatically positions the substrate on, and secures the substrate to, the substrate support. The substrate positioner typically includes feed rollers and may also include a cleaner roller to clean the data surface region as the substrate passes through the substrate feeder.

Other features and advantages will appear from the following description in which the preferred embodiments have been set forth in detail in conjunction with the accompanying drawings.

BRIEF DESCRIPTION OF THE DRAWINGS

FIGS. 2A, 2B and 2C are front, side, and rear elevational views of the substrate of FIG. 1;

FIG. 3 is a side view illustrating the shape of the opening in the card entry of FIG. 1;

FIG. 4A is a simplified schematic view illustrating the card entry, card sensor and first feed rollers of the substrate feeder of FIG. 1;

FIG. 4B illustrates the components of FIG. 4A with a card being inserted through the card entry and through the card sensor, which activates the first feed rollers which will then grip the card as the user continues to insert the card through the card entry;

DESCRIPTION OF THE PREFERRED EMBODIMENTS

Figure 1:
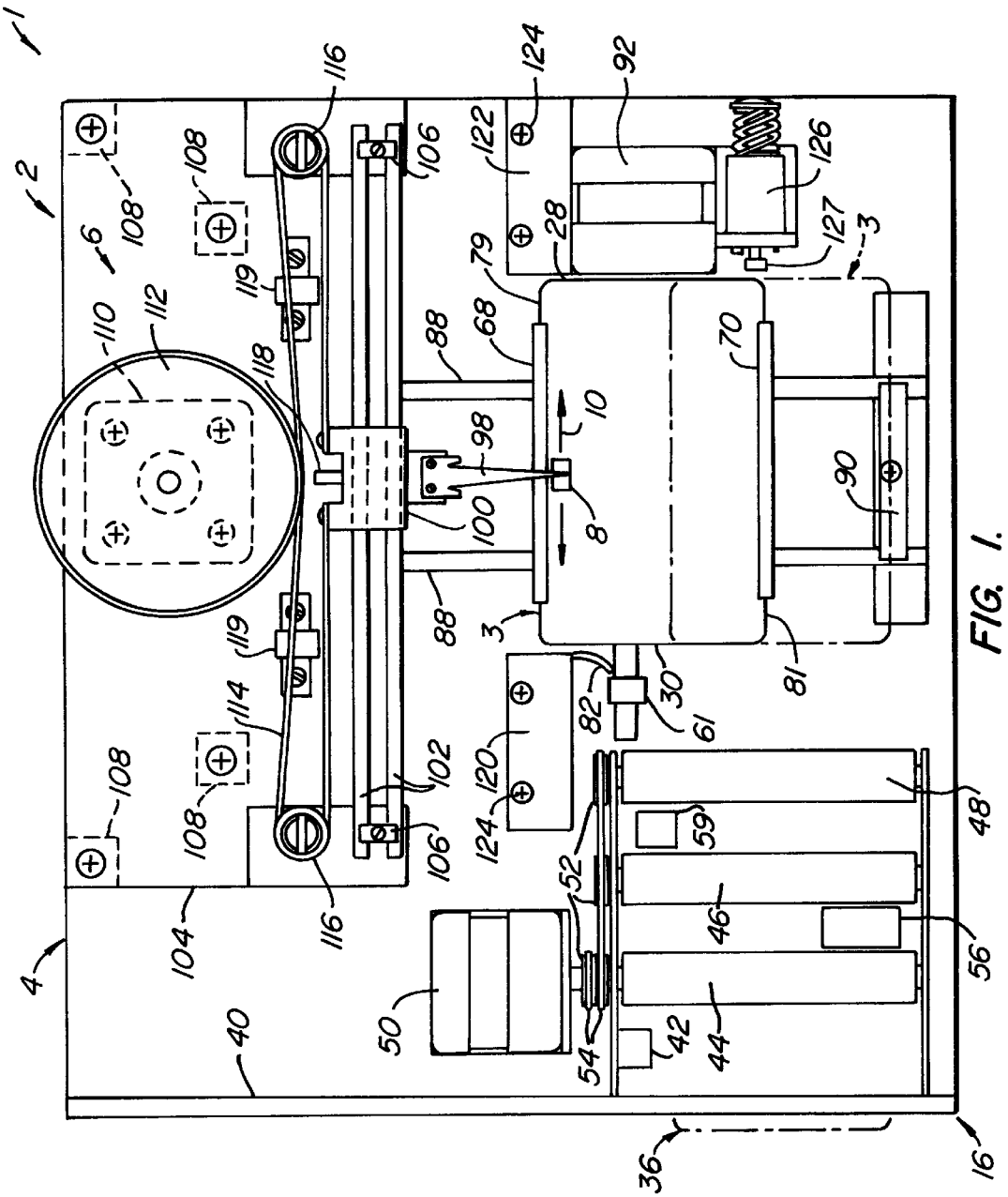
FIG. 1 is a simplified plan view of a data unit made according to the invention.

FIG. 1 illustrates, in a relatively simple schematic form, a data system 1 made according to the invention. Data system 1 comprises a data unit 2 and a substrate 3; substrate 3 is preferably in the form of a credit card-size card 3. Data unit 2 includes a base 4, which supports the various other components, a data head driver 6, which drives a data head 8 along a second path 10, a substrate or card support assembly 12, which moves card 3 or other substrate along a first path 14, and a substrate feeder 16, which drives card 3 to and from the substrate support assembly.

Card 3 is preferably a sandwich construction 0.51 mm (0.020 inch) thick ceramic core and upper and lower surfaces made of a suitable plastic material about 0.13 mm (0.005 inch) thick. FIG. 2A illustrates the front or bottom side 20 (relative to the figures) of card 3 having an embossed letter area 22 and a back, data or top side 24 having a data surface region 26 extending between first and second edges 28, 30 of the card.

Side 24 also preferably includes a magnetic, typically ferrous oxide, stripe 32 similar to that used with conventional credit cards. Data surface region 26 is preferably a magnetic region, and may also include ferrous oxide as a magnetic material. However, because of the use environment, to be discussed below, it is desired that region 26 be smooth and resistant to abrasion. This can be achieved in various conventional ways, such as by sputtering with carbon.

In the preferred embodiment of FIGS. 2A–2C, only a portion of side 24 is covered by data surface region 26. In some embodiments it may be desired to cover most or all of surface 24 with data surface region 26. A directional arrow 34 may also be included to aid the user in proper insertion of card 3 into card entry 36 shown in FIGS. 1, 3, 4A and 4B. As illustrated in FIG. 3, the opening 38 in card entry 36 has an enlarged portion to accommodate embossed letter area 22 shown in FIGS. 2A and 2B.

FIGS. 4A and 4B illustrate a portion of substrate feeder 16, including card entry 36 mounted to the front panel 40 of data unit 2. The user begins the read/write process by inserting a card 3 into opening 38 of card entry 36 sufficiently far to trip a light beam in a card sensor 42 which causes three sets of feed rollers 44, 46, and 48 to begin rotating as indicated by the arrows in FIGS. 4B and 5D. Feed rollers 44, 46, and 48 are driven by a feed system motor 50 through various pulleys 52 and belts 54. Once the user pushes card 3 far enough into unit 2 so that the first edge 28 of card 3 is captured at the nip of rollers 44, the feed rollers automatically move card 3 through substrate feeder 16 as suggested by FIGS. 5A–7A.

Figure 5A:
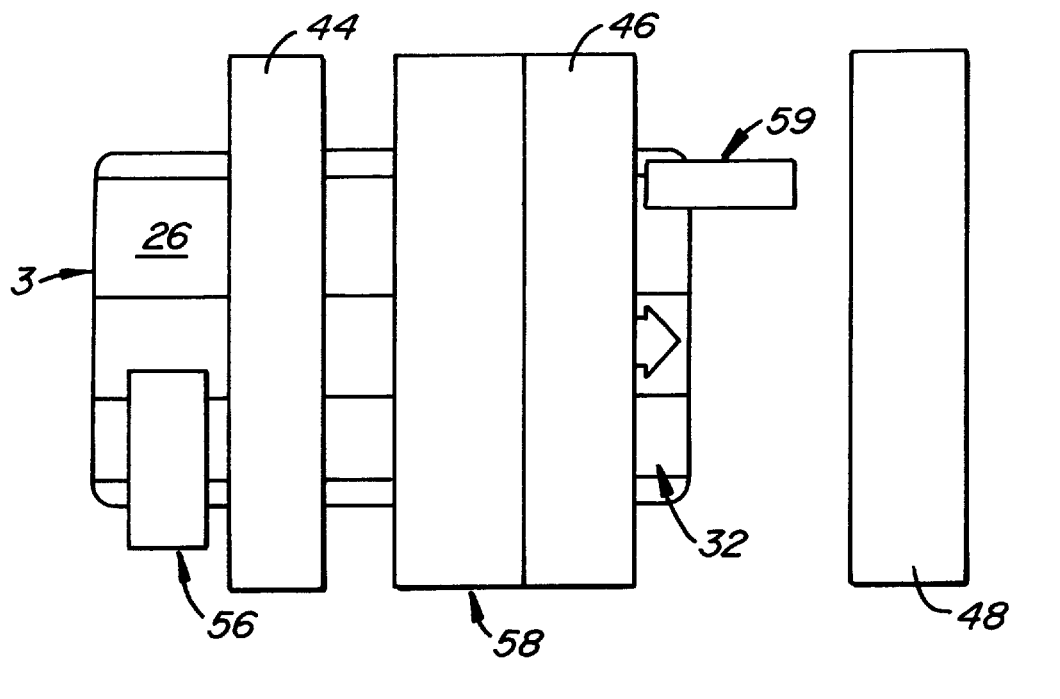
FIGS. 5A and 5B are top plan and side elevational views of a portion of the substrate feeder of FIG. 1, but also illustrating a counter-rotating cleaning roller, not shown in FIG. 1 for clarity, with the card engaged by the first and second sets of feed rollers and the upper surface of the card being cleaned by the counter-rotating cleaning roller.
Figure 5B:
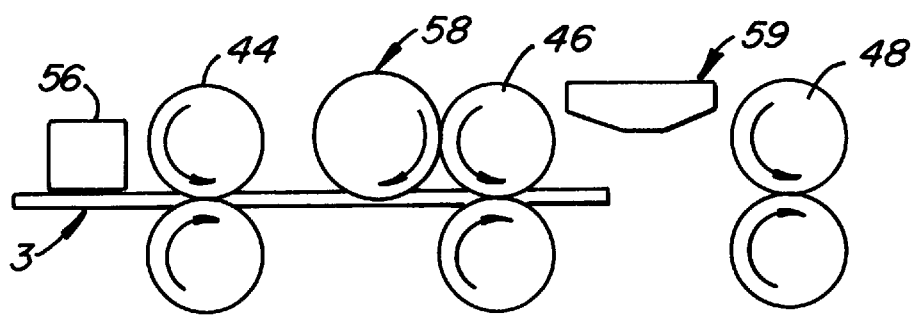

FIGS. 1, 5A and 5B illustrate the use of a magnetic stripe reader 56 which reads, in a conventional fashion, any information on magnetic stripe 32 as appropriate. Substrate feeder 16 also includes a counter-rotating cleaning roller 58. Cleaning roller 58 is not shown in FIG. 1 for clarity. Cleaning roller 58 is used to ensure that data surface region 26 is clean of particles and debris prior to being accessed by data head 8. Substrate feeder 16 also includes a reflective sensor 54 which senses the presence of data surface region 26. If card 3 has no data surface region 26, then feed rollers 44, 46 reverse the direction of card 3 and return it to the user with only magnetic stripe 32 having been read by magnetic stripe reader 56. Assuming card 3 includes a data surface region 26, feed rollers 44, 46, 48 continue the movement of card 3 past optical sensor 61 and towards card support 60 of card support assembly 12.

Figure 6A:
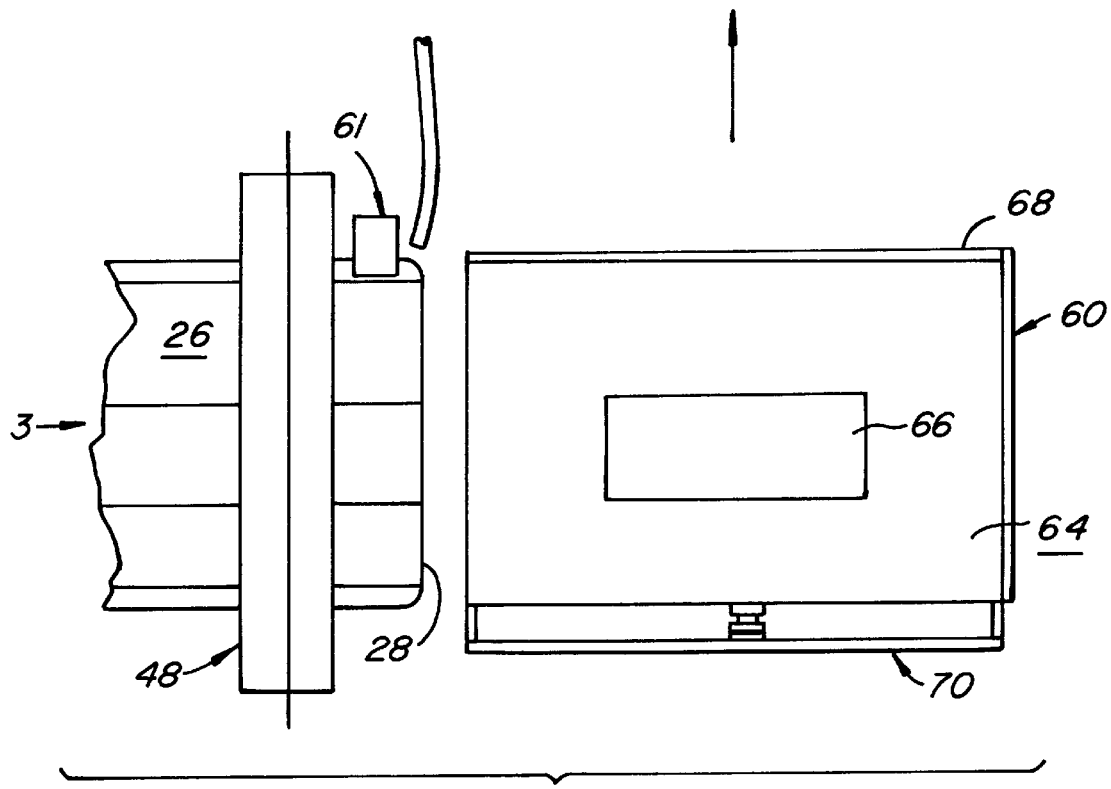
FIGS. 6A and 6B illustrate movement of the card between the third feed rollers, past a sensor and towards the card support of the card support assembly of FIG. 1.
Figure 6B:
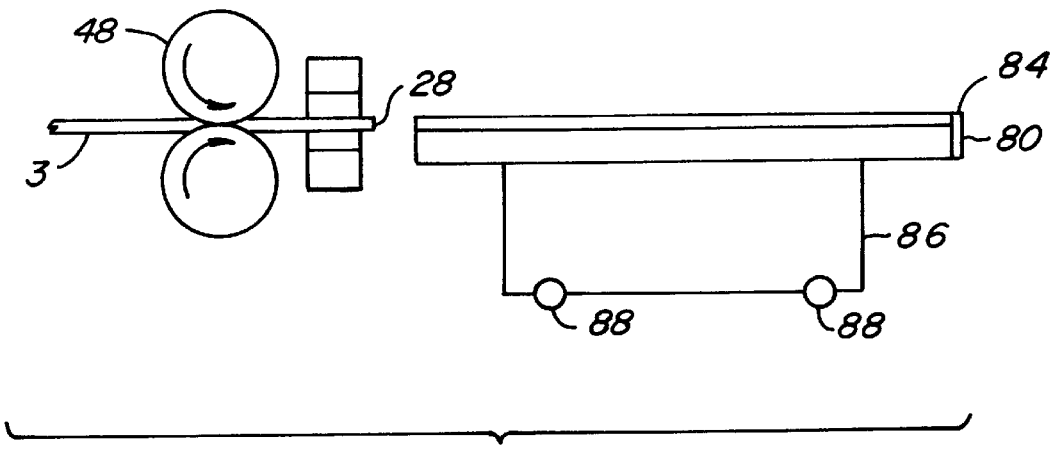
Figure 7A:
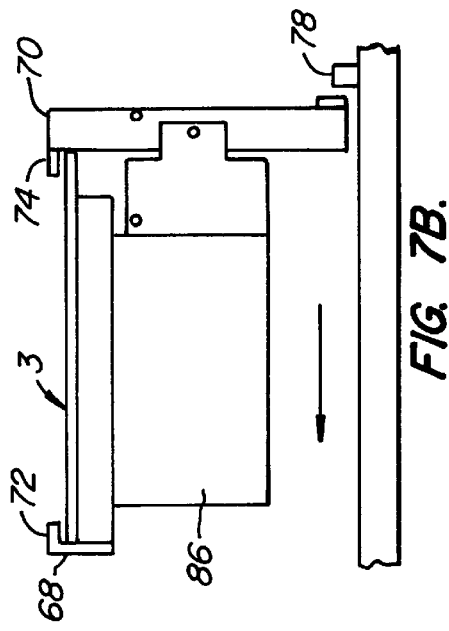
FIG. 7A is a simplified view illustrating the engagement of the bottom of a movable side registration member with a stud extending from the base when the card carriage, on which the card support is mounted, is at the load/unload position, the load/unload position being indicated by the card in dashed lines in FIG. 1.
Figure 7B:
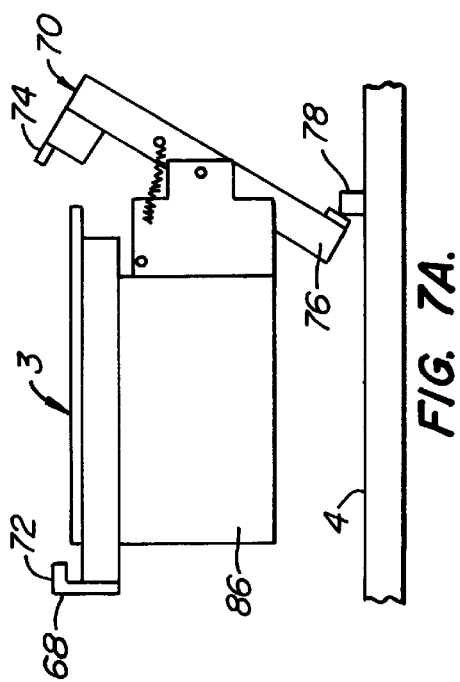
FIG. 7B illustrates the release of the movable side registration member as the carriage begins to move away from the load/unload position towards the solid line position of FIG. 1, thus capturing the third and fourth edges of the card between the movable and stationary side registration members.
Figure 9A:
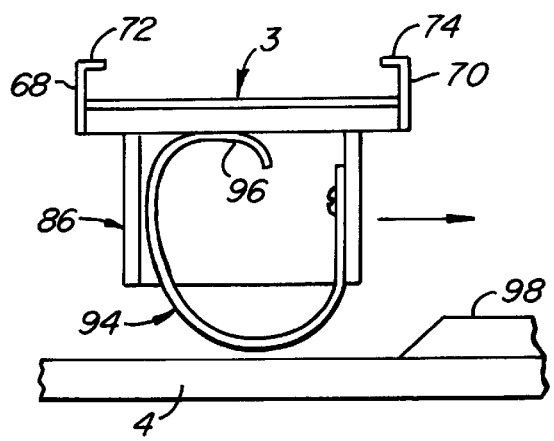
FIGS. 9A and 9B illustrate the movement of a vertically deflecting spring which engages the bottom of the card as the carriage moves towards the solid line position of FIG. 1, thus securing the card against the inwardly extending lips of the stationary and movable side registration members.
Figure 9B:
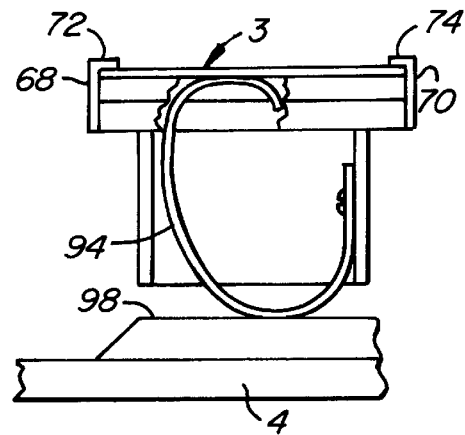

One end 62 of card support 60 is open to permit the free entry of card 3 onto the card support surface 64 of the card support. Card support surface 64 has an opening 66 formed through the middle of the surface as will be described below with reference to FIGS. 9A and 9B. Referring now also to FIGS. 7A and 7B, card support 60 is seen to include a stationary side registration member 68 and a movable side registration member 70. Members 68 and 70 have overhanging lips 72, 74. When card support 60 is in the load/unload position of FIGS. 6A, 6B and 7A, which corresponds to the dashed-line position of card 3 in FIG. 1, movable side registration member 70 is pivoted to its position of FIG. 7A by the engagement of the lower end 76 of member 70 with a stationary stud 78 extending upwardly from base 4. This permits card 3 to be freely driven onto surface 64 of card support 60 between registration members 68, 70. The initial movement of assembly 12 along path 14 towards data head driver 6 causes registration member 70 to engage a fourth edge 81 of card 3 and drive the third edge 79 of the card against registration member 68.

Figure 8A:
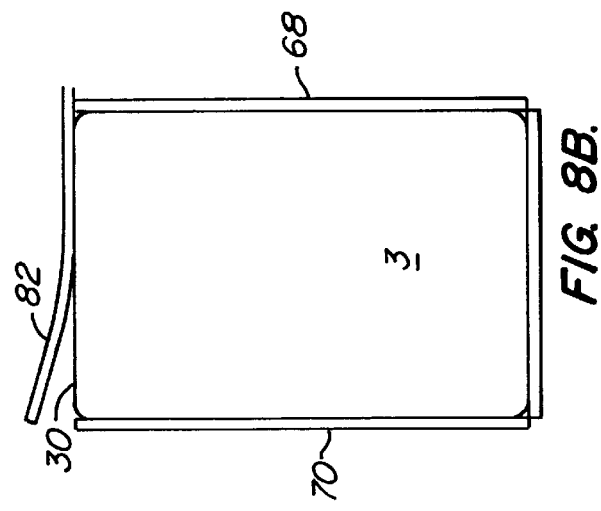
FIGS. 8A and 8B are plan views of the card support and card showing how the card guide of FIGS. 1 and 6A deflects the card into its fully loaded position as the carriage moves towards the solid line position of FIG. 1.
Figure 8B:
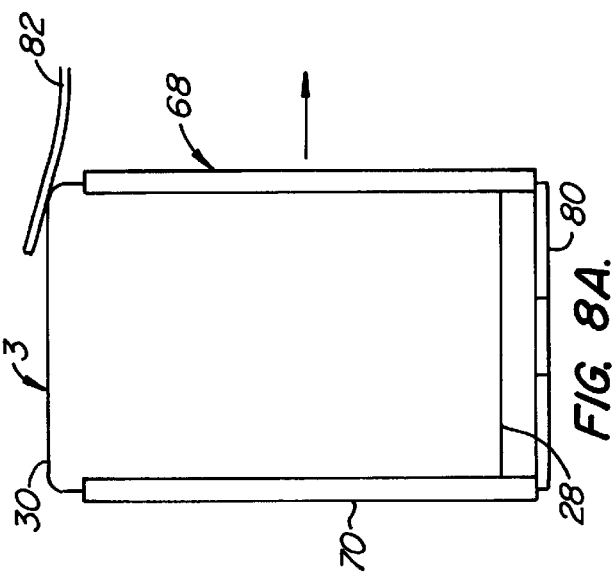

First edge 28 of card 3 is driven against abutment edge 80 of card support 60 by the movement of card support 60 along first path 14 towards data head driver 6, that is from the dashed-line position to the solid-line position of FIG. 1. Such movement along first path 14 causes second edge 30 of card 3 to engage an angled card guide 82 which drives card 3 fully onto card support 60 as shown in FIGS. 8A and 8B. Abutment edge 80 is sized so that its upper edge 84, see FIG. 6B, is slightly below, such as 0.38 mm (0.015 inch) below the top surface 24 of card 3 when the card is pressed upwardly to engage lips 72, 74 of members 68, 70 in the manner discussed below.

Card support 60 is mounted to and is carried by a carriage 86, the carriage being slidable along a pair of guide shafts 88, the guide shafts being supported on base 4 by shaft clamps 90, only one of which is shown in FIG. 1. Carriage 86, and thus card support 60 with card 3 thereon, is driven along first path 14 by a carriage motor 92.

The vertical movement or indexing of card 3 is achieved by the use of a C-shaped spring 94 mounted to the interior of carriage 86. An upper end 96 of spring 94 is aligned with and passes through opening 66 formed in card support surface 64 and illustrated in FIG. 6A. As carriage 86 moves along first path 14 from the load/unload position, corresponding to the dashed-line position of FIG. 1, towards data head driver 6, spring 94 rides up onto a cam 98 extending upwardly from base 4. This causes card 3 to be biased upwardly against lips 72, 74 and held in place against inadvertent movement during read/write operations.

Returning again to FIG. 1, card 3 is shown with data head 8 at track "000" position. Data head 8 is preferably of the magnetic head contact-type which contacts data surface region as data head 8 is moved along second path 10. Data head 8 is mounted to the distal end of an arm 98 which is mounted to a head carriage 100. Head carriage 100 is slidably mounted to a pair of guide shafts 102, the guide shafts mounted to a motor mount plate 104 by a pair of shaft clamps 106. Motor mount plate 104 is adjustably mounted to base 4 by four spacer mounts 108. Data head driver 6 also includes a read/write head motor 110 which drives a pulley 112 in alternating clockwise and counter-clockwise directions. Pulley 112 is coupled to carriage 100 by a drive band 114 which passes around a pair of roller bearings 116 as well as pulley 112.

The position of data head 8 relative to data surface region 18 is provided by the rotary position of pulley 112 and by a sensor interrupter 118 being sensed by a pair of sensors 119. Sensors 119 are generally aligned with edges 28, 30 of card 3 when the card is in the read/write position of FIG. 1.

Second path 10 extends beyond first and second edges 28, 30 onto data head support surfaces 120, 122. Data head support surfaces 120, 122 are generally coplanar with data surface region 18 so that data head 8 moves smoothly from region 18 onto support surfaces 120, 122. The use of support surfaces 120, 122 permits data head 8 to move across data surface region 18 at full speed. Preferably, data head 8 slows down, stops, reverses direction, and then speeds up for each subsequent pass while on one of data surfaces 120, 122. During this deceleration, stopping, reversal of direction, and acceleration, carriage motor 92 has a chance to index card 3 one track width along first path 14. Therefore, by the time data head 8 is ready to reengage data surface region 18, the next track, which may or may not be the adjacent track, is aligned with second path 10 and thus can be read by or written to by data head 8. Data head support surface 120, 122 are preferably low friction, low abrasion surfaces suitable for the sliding movement of data head 8 thereover. To ensure proper alignment, each data surface 120 is preferably provided with appropriate height adjusters 124. The gap between surfaces 120, 122 and card 3 is preferably small enough so that data head 8 traverses the gap smoothly. If necessary support at the gap can be provided by, for example, a small jet of air.

Figure 10:
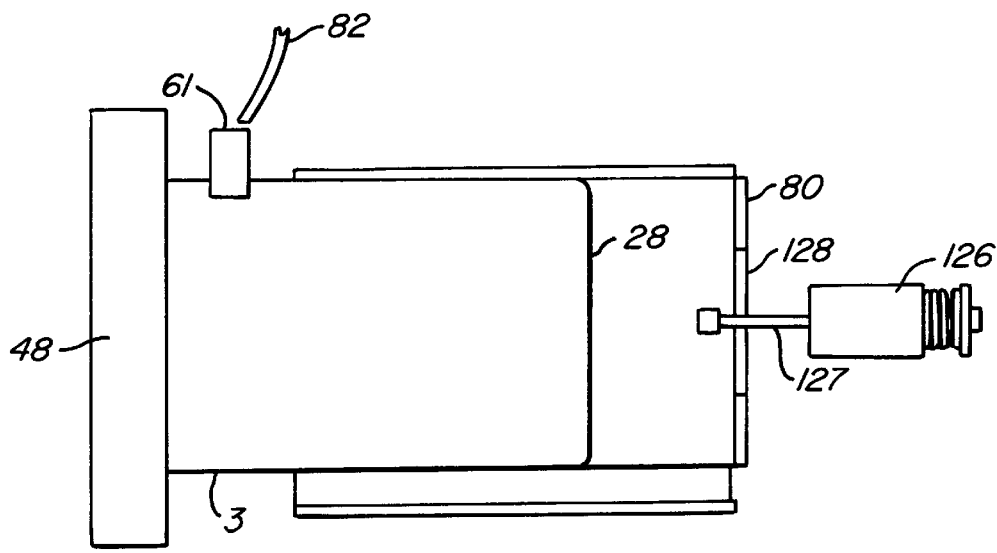
FIG. 10 illustrates the extension of the push solenoid of FIG. 1 used to cause the card to reengage with the third feed rollers once the card is returned to the load/unload of FIG. 7A position after a read/write procedure has been conducted.

Data head 8 is preferably at a rest position on data head support surface 120 or data head support surface 122 when card 3 is moved from a dashed-line to the solid-line positions of FIG. 1. This keeps data head 8 from contacting side registration member 68 during such movement. At the completion of read/write operations, carriage 86 moves to the load/unload position of FIGS. 7A and 10 whereupon a push solenoid 126 is actuated, see FIGS. 10, to push card 3 until the card is captured between third feed rollers 48. Push solenoid 126 has a plunger 127 which passes through a gap 128 in abutment edge 80 to engage first edge 28 of card 3. Feed rollers 44, 46 and 48, all rotating in the opposite direction indicated in FIG. 5B, drive card 3 back through opening 38 in card entry 36 to about the position of FIG. 4B.

In use, a user inserts a card 3 through opening 38 in card entry 36 whereupon substrate reader 16 drives it past magnetic stripe reader 56 and to reflective sensor 59. Assuming reflective sensor 59 senses the presence of data surface region 26, rollers 46, 48 continue driving card 3 towards substrate support assembly 12. After card 3 has passed third feed rollers 48, the inertia of the card causes the card to continue moving onto support surface 64 of card support 60. To ensure first edge 28 of card 3 abuts abutment edge 80 of card support 60, a card guide 82 is used to engage second edge 30 as card 3 moves from the load/unload position of FIG. 7A, that is the dash line position of FIG. 1, to the read/write position, that is the solid line position of FIG. 1. Third edge 79 of card 3 is driven against stationary side registration member 68 by the pivotal movement of spring biased side registration member 70 during the initial movement of the card from the dashed-line position toward the solid-line position of FIG. 1. Continued movement of card 3 toward the solid-line position of FIG. 1 causes spring 94 to be biased upwardly to drive card 3 upwardly until the lateral edges 79, 81 of the card engage lips 72, 74 of registration members 68, 70.

Once in the initial read/write position of FIG. 1, motor 110 drives data head 8 from one of data head support surfaces 120, 122 and data surface region 26 of card 3. In the preferred embodiment, motor 110 is designed to cause data head 8 to reach its desired speed of, for example, 318 cm per second (125 inches per second) by the time data head 8 reaches card 3. It is desired that information on data surface region 26 be written at the rate of 36,000 bits per inch or greater. The density of the recording is determined by several factors, including the uniformity in movement at which data head 8 passes over region 26, the construction of head 8, the construction of data surface region 6, the frequency of the read/write clock, and other conventional factors.

At the end of each pass, while data head 8 is moving over data head support surface 24 during its deceleration, stopping, reversal of direction, and acceleration, card 3 is indexed to the next track position to be accessed. If desired, the accessing of the track sequential or particular tracks can be selected, such as track 000, followed by track 023, followed by track 085, followed by track 031, etc. The organization of the data recorded on data surface region 26 is dependent largely by the controller selected. The controller for unit 2 may be of a conventional type, such as one made by Realtec of San Diego, Calif. and sold as product number TCNGE09. In one embodiment, 350 tracks, each track having 56 sectors with 256 bytes per sector for a total 5,017,600 bytes, will be used.

When it is desired to remove card 3 from the unit, data head 8 is parked on one of the two support surfaces 120, 122 and then motor 92 drives carriage 86 back to the load/unload position at which point push solenoid 126 is actuated. Plunger 127, which passes through gap 128 in abutment edge 80, pushes card 3 until card 3 is engaged by third rollers 48, at this time being rotated in directions opposite of the directions of FIGS. 5B and 6B. Card 3 is then delivered to the user in substantially the position as indicated in FIG. 4B.

In the preferred embodiment data head 8 physically contacts data surface region 26 and support surfaces 120, 122. It may be possible to use a so-called flying head in which data head 8 would not contact data surface region 26. However, it is believed that the gaps at edges 28,30 would create turbulence causing the flying head to crash onto data surface region 26. Also, the invention has been described with reference to magnetic, digitally encoded data. If desired, the data could be analog in nature and could be optical or magneto optical in character.

Figure 11:
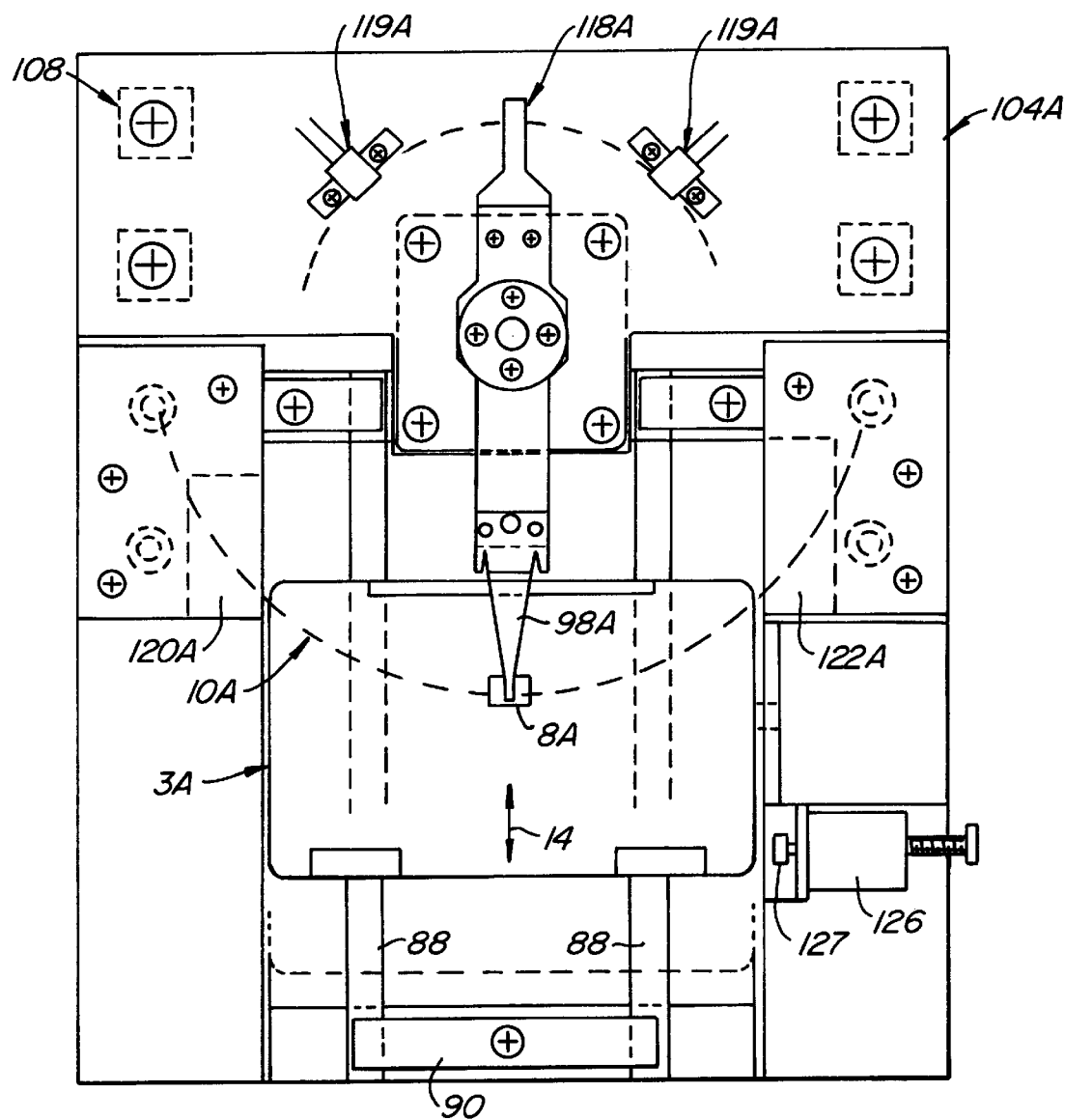
FIG. 11 is a simplified top plan view of a portion of an alternative embodiment of the invention in which the data head is mounted to the end of a pivotal arm which causes the read/write head to pass along an arcuate second path as opposed to the linear second path of the embodiment of FIG. 1.

FIG. 11 illustrates portions of an alternative embodiment of the invention with like reference numerals referring to like elements. In this case, data unit 2A uses an oscillating data head 8A which passes along an arcuate second path 10A. Data head support surfaces 120A, 122A are positioned somewhat differently, but provide the same service: support of data head 8A at each end of its movement. Sensors 119A indicate when data head 8 has passed from data surface region 26A so that data head 8 can begin its deceleration and reverse acceleration movement as card 3A is indexed along first path 14.

Other modifications and variation can be made to the disclosed embodiments without departing from the subject of the invention as defined in the following claims. For example, cleaning roller 58 could be replaced by or supplemented by an air vacuum head or a pressurized air nozzle to remove debris from data surface region 26.

What is claimed is:

1. A data unit, for use with a substrate having first and second edges and a data surface region therebetween, comprising:
    a base;
    a substrate support, configured to support a rectangular substrate having edges, mounted to the base for controlled movement along a first path;
    a substrate feeder configured to deliver a substrate to and remove the substrate from the substrate support;

a substrate positioner configured to position the substrate on and secure the substrate to the substrate support, the substrate positioner comprising lateral edge guides mounted to the substrate support and biased towards one another so a substrate positioned between the edge guides has its edges captured therebetween;

first and second data head support surfaces positioned at opposite ends of a second path and adjacent to said substrate support, said first and second paths being transverse to one another;

a data head drive mounted to the base, the data head drive comprising a data head reciprocally movable along the second path; and said data head comprising a data head surface which contacts said first and second data head support surfaces as said data head moves along the opposite ends of said second path.

2. The data unit according to claim 1 wherein the substrate support moves along the first path only.

3. The data unit according to claim 1 wherein said second path is an arcuate path.

4. The data unit according to claim 1 wherein said second path is a straight path.

5. A data unit, for use with a substrate having first and second edges and a data surface region therebetween, comprising:

a base;

a substrate support, configured to support a substrate mounted to the base for controlled movement along a first path;

a substrate feeder configured to deliver a substrate to and remove the substrate from the substrate support, the substrate feeder comprising feed rollers and at least one substrate cleaner roller;

a substrate positioner configured to position the substrate on and secure the substrate to the substrate support;

first and second data head support surfaces positioned at opposite ends of a second path and adjacent to said substrate support, said first and second paths being transverse to one another;

a data head drive mounted to the base, the data head drive comprising a data head reciprocally movable along the second path; and said data head comprising a data head surface which contacts said first and second data head support surfaces as said data head moves along the opposite ends of said second path.

6. The data unit according to claim 1 wherein said substrate positioner comprises means for separating the lateral edge guides when said substrate support is moved along the first track to a load/unload position so to permit a substrate to be freely mounted to or removed from the substrate support when at said load/unload position.

7. The data unit according to claim 1 wherein said lateral edge guides comprise overhanging lips configured to overlie a substrate when said edge guides engage said edges.

8. The data unit according to claim 7 wherein said overlapping lips comprise substrate engaging surfaces oriented generally coplanar with said data head support surfaces.

9. The data unit according to claim 1 wherein the substrate support comprises a first edge limit surface positioned to engage an edge of a substrate so to limit movement of the substrate onto the substrate support.

10. The data system according to claim 9 wherein the substrate positioner comprises an edge guide, mounted to the base, engagable with a second edge of a substrate so to move the substrate against the first edge limit surface as the substrate support is moved from a load/unload position, at which the substrate is mountable to and removable from the substrate support, towards a use position, at which the data head moves along the second path.

11. A data system comprising:

a substrate having first and second edges and a data surface region therebetween; and a data unit comprising:

a base;

a substrate support, supporting the substrate, mounted to the base for controlled movement along a first path;

first and second data head support surfaces positioned at opposite ends of a second path and adjacent to said first and second edges of said substrate, said first and second paths being transverse to one another;

a data head drive mounted to the base, the data head drive comprising a data head reciprocally movable along said second path; and said data head comprising a data head surface which contacts said data surface region and said first and second data head support surfaces as said data head moves along said second path.

12. The data system according to claim 11 wherein said substrate comprises outer layers bonded to a center layer.

13. A data system comprising:

a substrate having first and second edges and a data surface region therebetween;

said substrate comprising outer layers bonded to a center layer;

said outer layers comprising plastic material and the center layer comprising a ceramic material; and a data unit comprising:

a base;

a substrate support, supporting the substrate, mounted to the base for controlled movement along a first path;

first and second data head support surfaces positioned at opposite ends of a second path and adjacent to said first and second edges of said substrate, said first and second paths being transverse to one another;

a data head drive mounted to the base, the data head drive comprising a data head reciprocally movable along said second path; and said data head comprising a data head surface which contacts said data surface region and said first and second data head support surfaces as said data head moves along said second path.

14. A data system comprising:

a substrate having first and second edges and a data surface region therebetween;

said data surface region comprising nickel-cobalt; and a data unit comprising:

a base;

a substrate support, supporting the substrate, mounted to the base for controlled movement along a first path;

first and second data head support surfaces positioned at opposite ends of a second path and adjacent to said first and second edges of said substrate, said first and second paths being transverse to one another;

a data head drive mounted to the base, the data head drive comprising a data head reciprocally movable along said second path; and said data head comprising a data head surface which contacts said data surface region and said first and second data head support surfaces as said data head moves along said second path.

15. The data system according to claim 11 wherein said data surface region extends to both said first and second edges.

16. The data system according to claim 11 wherein the first and second data head support surfaces are generally coplanar with the data surface region.

17. The data system according to claim 11 wherein the data unit comprises a substrate handler comprising:
a substrate feeder which delivers the substrate to and removes the substrate from the substrate support; and
a substrate positioner, which properly positions the substrate on and secures the substrate to the substrate support.

18. The data system according to claim 17 wherein said substrate feeder comprises a data surface region sensor for sensing said data surface region.

19. The data system according to claim 18 wherein the substrate comprises a magnetic stripe region and the substrate reader comprises a magnetic stripe reader for reading information from the magnetic stripe region.

20. The data system according to claim 17 wherein said substrate support is configured to support a rectangular substrate having edges.

21. The data system according to claim 20 wherein substrate positioner comprises lateral edge guides mounted to the substrate support and biased towards one another so the substrate positioned between the edge guides has its edges captured therebetween.

22. The data system according to claim 21 wherein said substrate positioner comprises means for separating the lateral edge guides when said substrate support is moved along the first track to a load/unload position so to permit the substrate to be freely mounted to or removed from the substrate support when at said load/unload position.

23. A data system comprising:
a rectangular substrate having first and second edges and a data surface region therebetween; and
a data unit comprising:
a base;
a substrate support, supporting the substrate, mounted to the base for controlled movement along a first path;
a substrate feeder which delivers the substrate to and removes the substrate from the substrate support;
a substrate positioner, which properly positions the substrate on and secures the substrate to the substrate support, comprising lateral edge guides mounted to the substrate support and biased towards one another so the substrate positioned between the edge guides has its edges captured therebetween;
first and second data head support surfaces positioned at opposite ends of a second path and adjacent to said first and second edges of said substrate, said first and second paths being transverse to one another;
a data head drive mounted to the base, the data head drive comprising a data head reciprocally movable along said second path; and
said data head comprising a data head surface which contacts said data surface region and said first and second data head support surfaces as said data head moves along said second path.

24. The data system according to claim 23 wherein said substrate positioner comprises means for biasing a substrate against the overhanging lips to position the data surface region to be generally coplanar with the acceleration surfaces.

25. The data system according to claim 17 wherein the substrate support comprises a first edge limit surface positioned to engage an edge of the substrate so to limit movement of the substrate onto the substrate support.

26. The data system according to claim 25 wherein the substrate positioner comprises an edge guide, mounted to the base, engagable with a second edge of a substrate so to move the substrate against the first edge limit surface as the substrate support is moved from a load/unload position, at which the substrate is mountable to and removable from the substrate support, towards a use position, at which the data head moves along the second path and contacts the data surface region.

* * * * *